(12) United States Patent
Zhernosekov et al.

(10) Patent No.: US 9,142,328 B2
(45) Date of Patent: Sep. 22, 2015

(54) MOLECULE FOR FUNCTIONALIZING A SUPPORT, ATTACHMENT OF A RADIONUCLIDE TO THE SUPPORT AND RADIONUCLIDE GENERATOR FOR PREPARING THE RADIONUCLIDE, AND PREPARATION PROCESS

(75) Inventors: Konstantin Zhernosekov, Garching (DE); Tuomo Nikula, Ottobrunn (DE)

(73) Assignee: ITM ISOTOPEN TECHNOLOGIEN MÜNCHEN AG, Garching (DE)

( * ) Notice: Subject to any disclaimer, the term of this patent is extended or adjusted under 35 U.S.C. 154(b) by 1105 days.

(21) Appl. No.: 12/700,478

(22) Filed: Feb. 4, 2010

(65) Prior Publication Data

US 2010/0202915 A1 Aug. 12, 2010

(30) Foreign Application Priority Data

Feb. 6, 2009 (DE) .......................... 10 2009 007 799

(51) Int. Cl.
G21H 5/02 (2006.01)
(52) U.S. Cl.
CPC ...................... *G21H 5/02* (2013.01)
(58) Field of Classification Search
CPC ...................................................... G21H 5/02
See application file for complete search history.

(56) References Cited

U.S. PATENT DOCUMENTS

| | | | |
|---|---|---|---|
| 3,774,036 A | 11/1973 | Gerhart | |
| 4,333,911 A | 6/1982 | Comar et al. | |
| 5,384,229 A * | 1/1995 | Pai et al. | 430/270.1 |
| 7,011,816 B2 | 3/2006 | Griffiths et al. | |
| 7,023,000 B2 | 4/2006 | Zyuzin | |
| 7,728,310 B2 * | 6/2010 | Fitzsimmons et al. | 250/432 PD |
| 7,794,691 B2 * | 9/2010 | Morgenstern et al. | 424/1.81 |

FOREIGN PATENT DOCUMENTS

| | | |
|---|---|---|
| DE | 2932948 | 2/1981 |
| FR | 2899585 | 4/2006 |
| GB | 1532225 | 11/1978 |
| GB | 2056471 | 3/1981 |
| WO | WO 2005/089912 | 9/2005 |

OTHER PUBLICATIONS

Grant & Hackh's Chemical Dictionary (5th Ed. 1987) at page 148.*
Al-Nahhas, A. et al., "Gallium-68 PET: A New Frontier in Receptor Cancer Imaging", Anticancer Research, vol. 27, No. 6B, pp. 4087-4094, 2007.
Maecke et al., "Ga-Labeled Peptides in Tumor Imaging", The Journal of Nuclear Medicine, vol. 46, No. 1 (Suppl), pp. 172S-178S, Jan. 2005.
Breeman et al., "Radiolabelling DOTA-peptides with $^{68}$Ga", European Journal of Nuclear Medicine and Molecular Imaging, vol. 32, No. 4, pp. 478-485, Apr. 2005.
Meyer et al., "$^{68}$Ga-labelled DOTA-derivatised peptide ligands", European Journal of Nuclear Medicine and Molecular Imaging, vol. 31, No. 8, pp. 1097-1104, Aug. 2004.
Zhernosekov et al., "Processing of Generator-Produced $^{68}$Ga for Medical Application", The Journal of Nuclear Medicine, vol. 48, No. 10, pp. 1741-1748, Oct. 2007.
Schuhmacher et al., "A New $^{68}$Ge/$^{68}$Ga Radioisotope Generator System for Production of $^{68}$Ga in Dilute HCl*", International Journal of Applied Resolution and Isotopes, vol. 32, pp. 31-36, Apr. 1980.
Al-Nahhas et al.,"Gallium-68 PET: A New Frontier in Receptor Cancer Imaging", Anticancer Research, vol. 27, No. 6B, pp. 4087-4094, 2007.

* cited by examiner

*Primary Examiner* — Samantha Shterengarts
(74) *Attorney, Agent, or Firm* — Pearl Cohen Zedek Latzer Baratz LLP

(57) ABSTRACT

Molecule for attaching a radioactive parent nuclide to a support, comprising at least one functional group for attaching the radioactive parent nuclide; and a molecular moiety suitable for establishing a nonpolar bond to the support.

12 Claims, 1 Drawing Sheet

Figure 1A:
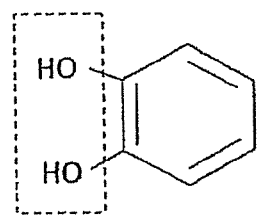

MOLECULE FOR FUNCTIONALIZING A SUPPORT, ATTACHMENT OF A RADIONUCLIDE TO THE SUPPORT AND RADIONUCLIDE GENERATOR FOR PREPARING THE RADIONUCLIDE, AND PREPARATION PROCESS

CROSS-REFERENCE TO RELATED APPLICATIONS

This application claims priority under 35 U.S.C. §119 of German Patent Application, 10 2009 007 799.5, filed Feb. 6, 2009, which is incorporated herewith by reference in its entirety.

BACKGROUND OF THE INVENTION

The invention relates to a molecule for functionalizing the surface of an inert support and to the use in the preparation of a radionuclide of high purity in a generator. The invention relates in particular to a molecule for attaching a radioactive parent nuclide, in particular germanium-68, to a support.

Radionuclides, in particular positron emitters, are used in positron emission tomography (PET). In the PET examination of a patient, the distribution of a weakly radioactive, positron emitter-labelled substance such as, for example, a biomolecule is visualized in an organism via the radioactive disintegration of the positron emitter, using a detector.

Since biomolecules participate in the normal metabolism of the organism, accumulating in the process inter alia in tumour cells, PET can be utilized for identifying tumour cells.

One example of a radionuclide preferred for PET is gallium-68, which can be obtained using a germanium-68/gallium-68 radionuclide generator system (1, 2). With a half-life of 67.63 minute's, the isotope gallium-68 disintegrates with emission of a positron. By virtue of its physical and chemical properties, gallium-68 is highly suitable for nuclear medical examinations. Owing to its short half-life, it is particularly suitable for radiolabelling biomolecules.

Gallium-68 can be generated by radioactive disintegration from the parent nuclide germanium-68 which disintegrates with a half-life of 270.8 days.

In the generator, the germanium-68 is attached to an insoluble matrix of an inert support, where, by continuous disintegration of the germanium, gallium-68 is constantly formed and may be extracted from the generator by elution with a solvent.

The radionuclides used for labelling the radio-pharmaceutics have to meet high quality standards. In particular, the radionuclides generated have to have a high degree of purity and must be free from metallic impurities since these may, owing to competing reactions, have an adverse effect on the labelling of the radiopharmaceutics, and may reduce the technically achievable yield (3-5).

As support for the stationary phase, known germanium-68/gallium-68 generator systems use inorganic ion exchange substances, such as, for example, $TiO_2$, $SnO_2$, $Al(OH)_3$. However, in a disadvantageous manner, the gallium-68 extracted therewith contains metallic impurities, such that the original eluate has to be purified prior to use in a radiopharmaceutic (4, 5).

As an alternative to inorganic ion exchange substances, generators use, as supports, organic polymers to which, with the aid of functional groups, individual molecules having a high affinity for germanium are attached. Such molecules may, for example, be pyrogallol or catechol which, via phenolic hydroxyl groups, form stable complexes with germanium (FIG. 1A) (6).

In a known germanium-68/gallium-68 generator, the support used is a resin prepared from pyrogallol and formaldehyde (4-7). During the preparation of the germanium-specific resin, pyrogallol is immobilized on the support by copolymerization with formaldehyde.

However, the applicability of these materials and generator systems is limited.

Thus, with the germanium-68/gallium-68 generators mentioned above based on organic polymer, gallium-68 can be obtained only in concentrated acid solutions (3-6M). This requires reprocessing of the eluate prior to use as radiopharmaceutic.

In addition, the process for synthesizing the pyrogallol/formaldehyde resin is technically very demanding and expensive. In addition, the main component of the formaldehyde matrix is toxic, such that the preparation of an injectable radiopharmaceutic requires additional purification steps.

OBJECTS OF THE INVENTION

It was an object of the present invention to provide a substance for preparing a radionuclide using a generator, where a radionuclide can be attached to a support which can be used as stationary phase in the generator, and which allows the radionuclide to be prepared with a high degree of purity and without impurities, and also a corresponding generator and a preparation process.

The object is achieved by a molecule having the features according to claim 1.

DETAILED DESCRIPTION OF THE INVENTION

According to the invention, a molecule for attaching a radioactive, parent nuclide to a support is provided which comprises at least one functional group for attaching the radioactive parent nuclide and a molecular moiety suitable for establishing nonpolar bonds to the support.

By virtue of the nonpolar bond to the support, in an aqueous solution which can be used for eluting the daughter nuclide in a generator, the radioactive parent nuclide cannot be detached from the support material. It is thus possible to avoid contamination of the eluate, and to extend the lifespan of the generator for subsequent elutions.

The radioactive parent nuclide may comprise germanium-which disintegrates to gallium-68. It is thus possible to provide a support for a germanium-68/gallium-68 generator which allows the preparation of highly pure gallium-68 substantially without impurities, in particular metallic impurities, and with a high degree of purity and preferably without further preparation steps prior to use in a radiopharmaceutic. The degree of purity that can be achieved is preferably less than 1 ppm, with preference less than 100 ppb, particularly preferably less than 10 ppb or even less than 1 ppb of impurities.

According to one embodiment, the functional group for attaching the parent nuclide comprises a hydroxyl group and preferably a phenolic hydroxyl group. The molecule may also comprise a plurality of functional groups such as, for example, two, three or more functional groups. With the aid of the functional group, which has a high affinity to germanium, thus allowing quantitative adsorption of the germanium from the liquid phase, it is possible to form stable complexes with germanium molecules.

According to a preferred embodiment, the parent nuclide is germanium-68 and the functional group is pyrogallol or catechol.

According to a further preferred embodiment, the molecular moiety suitable for establishing a nonpolar bond to the support is hydrophobic. Using a hydrophobic molecular moiety, the molecule can be attached via a nonpolar bond to an inert support or be immobilized thereon, preventing inter alia a dissolution of the molecule and the parent nuclide attached thereto in an aqueous solution.

In contrast, known compounds having one or more germanium-specific functional groups such as, for example, catechol and pyrogallol, are highly soluble in aqueous solutions. It is not possible to attach catechol and pyrogallol directly to an inert support such that the bond withstands extraction of the daughter nuclide from the generator using an aqueous solution. The solubility in water of catechol and pyrogallol is 450 g/l and 400 g/l, respectively.

Using derivatives of molecules which, in addition to at least one germanium-specific functional group, additionally have a hydrophobic molecular moiety, it is possible to achieve insolubility in water.

According to a further preferred embodiment, the hydrophobic molecular moiety is selected from the group consisting of:
(i) aromatic and heteroaromatic moieties, such as, for example, benzene, naphthalene, quinoline;
(ii) saturated or unsaturated fatty acids having more than 3 carbon atoms, preferably from 3 to 20 carbon atoms;
(iii) branched or straight-chain alkyl chains having more than 3 carbon atoms, such as, for example, octyl, decyl, or octadecyl groups, preferably having from 3 to 20 carbon atoms.

According to a preferred embodiment, the molecule is an organic molecule selected from the group consisting of 2,3-dihydroxynaphthalene and dodecyl 3,4,5-trihydroxy-benzoate.

According to a further preferred embodiment, the support is selected from the group consisting of an organic support and an inorganic support, such as, for example, silica gel.

The invention furthermore provides a support for use as stationary phase, comprising at least one molecule according to the invention according to any of the embodiments described above and which is attached to the support via a nonpolar bond.

The invention furthermore provides a generator for a radioactive daughter nuclide, in particular gallium-68, comprising a molecule according to the invention according to any of the embodiments described above, a support, the molecule being attached to the support via a nonpolar bond, and a parent nuclide, in particular germanium-68, which is attached to the molecule via the functional group.

The invention furthermore provides a process for preparing a radioactive daughter nuclide which comprises the following steps: providing a generator comprising a support and a parent nuclide to which a molecule according to the invention according to any of the embodiments described above is attached, where the molecule is attached to the support via a nonpolar bond, and eluting the daughter nuclide.

Using the generator according to the invention, it is possible to prepare gallium-68 with a particularly high degree of purity, metallic impurities and other residues from the generator being substantially avoidable. The generator can be prepared with low expense and in a cost-effective manner.

According to a further preferred embodiment, the process comprises charging the generator with silica gel as support, to which silica gel the molecule is applied.

According to yet another embodiment, the process comprises bringing the support into contact with the parent nuclide in a solution. Suitable solvents are the following substances: water, aqueous acids, solutions, salt solutions, such as, for example, buffer solutions, organic solutions based on alcohol, ether, etc.

According to a further preferred embodiment, the parent nuclide may comprise germanium-68 which disintegrates to gallium-68.

Finally, the invention comprises the use of a molecule according to any of the embodiments indicated above for preparing pure gallium-68.

Figure 2A:
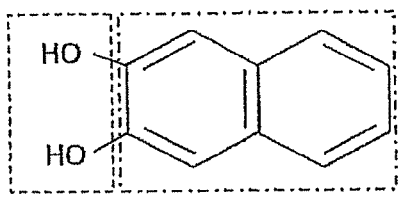
Figure 2B:
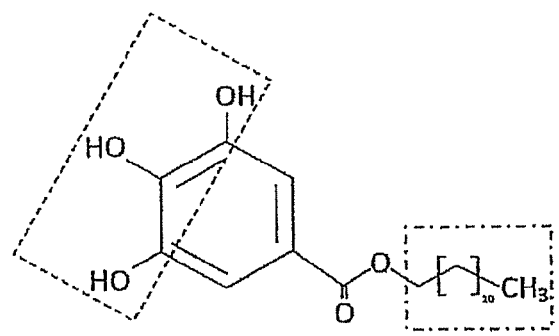

FIGS. 1a, b show the structural formulae of catechol (FIG. 1a) and pyrogallol as compounds having germanium-specific functional groups;

FIGS. 2a, b show the structural formulae of examples of molecules according to the invention such as 2,3-dihydroxynaphthalene (FIG. 2a) and dodecyl 3,4,5-trihydroxybenzoate.

EXAMPLE

Figure 1B:
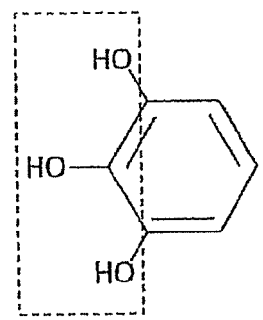

A germanium-specific resin was prepared by coating inert silica gel with dodecyl 3,4,5-trihydroxybenzoate having the structural formula shown in FIG. 1b. The resin was used for preparing small chromatographic columns. An aqueous solution comprising the radio-nuclide germanium-68 having an activity in the range between 20 and 1250 MBq was then pumped through the columns. During this step, the germanium-68 was adsorbed quantitatively on the columns.

The columns charged with germanium-68 were then used to prepare the short-lived gallium-68. It was possible to repeatedly elute the gallium-68 generated by the germanium-68 absorbed on the support. The elution of gallium-68 was effected using weak hydrochloric acid solutions (0.05 M HCl) having a low volume of up to 2.5 ml. Leakage of the parent nuclide germanium-68 was in the range $1\times10^{-4}$–$3\times10^{-3}$%. The gallium-68 could be used directly and without further chemical reprocessing for preparing injectable gallium-68 radio-pharmaceutics.

Literature References:
1) Al-Nahhas A, Win Z, Szysko T, Singha A, Nannil C, Fanti S, Rubello D. Gallium-68 PET: A New Frontier in Receptor Cancer Imaging. Anticancer research. 2007; 27: 4087-4094
2) Helmut M, Hofmann M, Haberkorn U. $^{68}$Ga-Labeled Peptides in Tumor Imaging. J Nuc Med. 2005; 46: 172S-178S
3) Breeman W, Jong M, Blois E, Bernard B, Konijnenberg M, Krenning E. Radiolabelling DOTA-peptides with $^{68}$Ga. Eur J Nuc Med Mol Imaging. 2005; 32: 478-458
4) Meyer G-J, Mäcke H, Schuhmacher J, Knapp W, Hofmann M. $^{68}$Ga-labelled DOTA-derivatised peptide ligands. Eur J Nuc Med Mol Imaging. 2004; 31: 1097-1104
5) Zhernosekov K, Filosofov D, Baum R, Aschoff P, Bihl H, Razbash A, Jahn M, Jennewein M, Rösch F. Processing of generator-produced $^{68}$Ga for medical application. J Nuc Med. 2007; 48: 1741-1748
6) Patent DE 29 32 948 A1
7) Schuhmacher J, Maier-Borst W. A new $^{68}$Ge/$^{68}$Ga radio-isotope generator system for production of $^{68}$Ga in dilute HCl. I J Appl Rad Isotopes. 1981; 32: 31-36

The invention claimed is:
1. A generator for a radioactive daughter nuclide comprising
a compound consisting of one of a group consisting of pyrogallol and catechol, and one of a group consisting of a saturated or unsaturated fatty acid having more than 3 carbon atoms, and a branched or straight-chain alkyl chain having more than 3 carbon atoms;
a support selected from the group consisting of an organic support and an inorganic support comprising resin and silica gel, the compound being attached to the support via a nonpolar bond formed between the one of the group consisting of a saturated or unsaturated fatty acid having more than 3 carbon atoms, and a branched or straight-chain alkyl chain having more than 3 carbon atoms, and the support; and
a parent nuclide, which is attached to the one of the group consisting of pyrogallol and catechol.

2. The generator according to claim 1, where the compound is dodecyl 3,4,5-trihydroxybenzoate.

3. The generator according to claim 1, wherein the branched or straight-chain alkyl chain having more than 3 carbon atoms is one of an octyl, decyl or octadecyl groups.

4. The generator according to claim 1 wherein said radioactive daughter nuclide is gallium-68 and said parent nuclide is germanium-68.

5. A generator for a radioactive daughter nuclide, comprising:
a compound consisting of dodecyl 3,4,5-trihydroxybenzoate or 2 3-dihydroxynaphthalene;
a support, the compound being attached to the support via a nonpolar bond; and
a parent nuclide, which is attached to the compound via a functional group of the compound.

6. The generator according to claim 5, where the functional group of the compound comprises a hydroxyl group or a phenolic hydroxyl group.

7. The generator according to claim 5, where the functional group of the compound is pyrogallol or catechol.

8. The generator according to claim 5, where the support is selected from the group consisting of an organic support and an inorganic support comprising resin and silica gel.

9. The generator according to claim 8, where the silica gel is coated with the compound.

10. The generator according to claim 5, where the nonpolar bond is established by a molecular moiety of the compound.

11. The generator according to claim 10, where the molecular moiety is hydrophobic.

12. The generator according to claim 10, where the hydrophobic molecular moiety is selected from the group consisting of:
an aromatic or heteroaromatic moiety;
a saturated or unsaturated fatty acid having more than 3 carbon atoms; and
a branched or straight-chain alkyl chain having more than 3 carbon atoms.

* * * * *

UNITED STATES PATENT AND TRADEMARK OFFICE
CERTIFICATE OF CORRECTION

| | |
|---|---|
| PATENT NO. | : 9,142,328 B2 |
| APPLICATION NO. | : 12/700478 |
| DATED | : September 22, 2015 |
| INVENTOR(S) | : Konstantin Zhernosekov et al. |

It is certified that error appears in the above-identified patent and that said Letters Patent is hereby corrected as shown below:

Specification

In column 2, at lines 48-49, the issued US patent should read as follows:

-- The radioactive parent nuclide may comprise germanium-68 which disintegrates to gallium-68. --

Signed and Sealed this
Fourteenth Day of June, 2016

Michelle K. Lee
*Director of the United States Patent and Trademark Office*